United States Patent
Spahn

(10) Patent No.: US 7,580,554 B2
(45) Date of Patent: Aug. 25, 2009

(54) METHOD FOR DETERMINING ORGAN-DEPENDENT PARAMETERS FOR IMAGE POST-PROCESSING AND IMAGE PROCESSING DEVICE

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 692 days.

(21) Appl. No.: 11/311,586

(22) Filed: Dec. 15, 2005

(65) Prior Publication Data

US 2006/0133658 A1      Jun. 22, 2006

(30) Foreign Application Priority Data

Dec. 17, 2004   (DE) .................... 10 2004 060868

(51) Int. Cl.
   *G06K 9/00*      (2006.01)
   *A61B 5/00*      (2006.01)
(52) U.S. Cl. ................. 382/128; 382/209; 600/300
(58) Field of Classification Search ........... 382/100, 382/128, 129, 130, 131, 132, 133, 134, 154, 382/155, 168, 171, 173, 181, 190, 192, 195, 382/224, 232, 260, 274, 276, 209, 219; 706/12, 706/20; 600/300; 378/2, 21, 23
See application file for complete search history.

(56) References Cited

U.S. PATENT DOCUMENTS

| | | | | |
|---|---|---|---|---|
| 5,509,084 A | * | 4/1996 | Tanaka | 382/128 |
| 5,935,060 A | * | 8/1999 | Iliff | 600/300 |
| 6,097,833 A | * | 8/2000 | Lobregt et al. | 382/130 |
| 7,117,188 B2 | * | 10/2006 | Guyon et al. | 706/20 |
| 7,187,790 B2 | * | 3/2007 | Sabol et al. | 382/128 |
| 7,318,051 B2 | * | 1/2008 | Weston et al. | 706/12 |

FOREIGN PATENT DOCUMENTS

DE       198 12 749 A1     9/1999

OTHER PUBLICATIONS

J. A. Ware, I. Ciuca; "A Neural Network Based Integrated Image Processing Environment for Object Recognition in Medical Applications"; Tenth IEEE Symposium on Computer-Based Medical Systems; Jun. 11-13, 1997; pp. 149-154.

* cited by examiner

*Primary Examiner*—Seyed Azarian

(57) ABSTRACT

Method for determining organ-dependent parameters for image post-processing and image processing device The invention relates to a method for the automatic determination of one or more organ-dependent parameters for image post-processing, having the following steps:
   recording of a raw image and the execution of image preprocessing on the raw image data in order to generate a preprocessed image,
   determination of an organ-specific comparison image, stored in a database, which has been optimized by postprocessing using organ-specific postprocessing parameters, and acquisition of the postprocessing parameters for the comparison image, and
   postprocessing of the preprocessed raw image, using the postprocessing parameters of the comparison image.

10 Claims, 1 Drawing Sheet

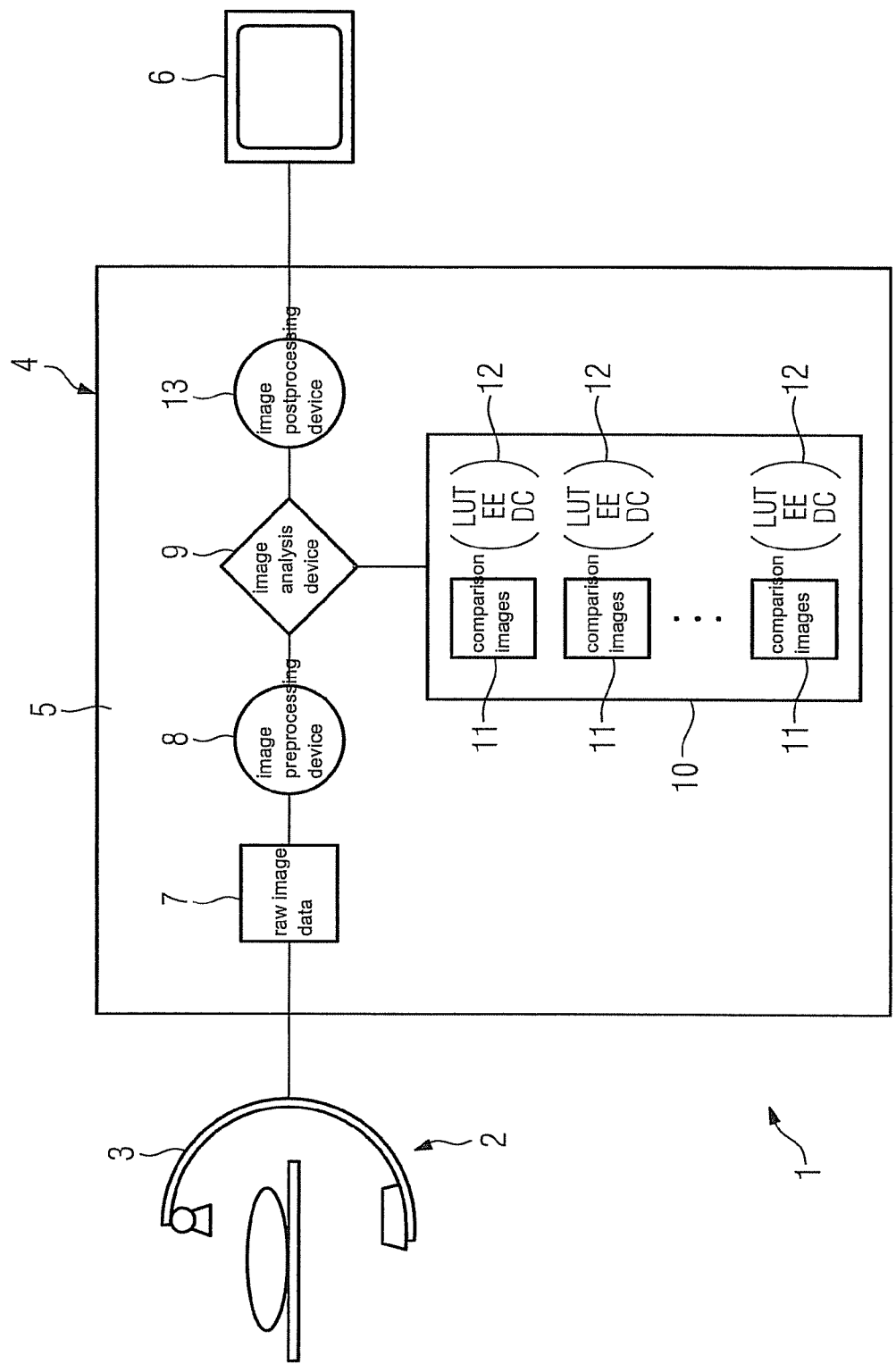

METHOD FOR DETERMINING ORGAN-DEPENDENT PARAMETERS FOR IMAGE POST-PROCESSING AND IMAGE PROCESSING DEVICE

CROSS REFERENCE TO RELATED APPLICATIONS

This application claims priority to the German application No. 10 2004 060 868.7, filed Dec. 17, 2004 which is incorporated by reference herein in its entirety.

FIELD OF INVENTION

The invention relates to a method for the automatic determination of one or more organ-dependent parameters for image post-processing, together with an image processing device for carrying out the method.

BACKGROUND OF INVENTION

Digital imaging methods play an ever more important role in medical diagnosis. Whereas digital techniques have been used from the beginning in such diagnostic methods as, for example, computer tomography, magnetic resonance, ultrasound and nuclear medical methods, a transition to digital imaging is currently taking place on a large scale in "conventional" X-ray methods such as radiography, mammography, angiography or cardiology, in particular with the assistance of solid state radiation detectors or planar detectors.

In general, the image processing this involves is becoming ever more complex, to show optimally the diagnostic content of the image. For example, methods are being used which suppress the noise, improve the sharpness on a frequency-selective basis, reduce the proportions of stray radiation, reduce coarse contrasts, use signal-dependent filtering methods etc. Common to the image processing algorithms in these cases is the fact that the complex methods require more and more parameters to be selected for optimal image processing. For the various organs, projections, patient-specific parameters (such as age, gender, weight) and possibly other external conditions, there are in each case additional ideal image processing parameters. The large number of image processing parameters, on the one hand, and on the other hand organ-specific parameters, opens up a large field of so-called "organ programs", which must be preset before the image is recorded. These organ programs generally contain a set of previously-defined image postprocessing parameters, relating to a specific object under examination, that is an organ in the widest sense, where the term "organ" refers not only to organs in the common sense, but also any other structure of a body, such as a knee, a tissue etc.

In view of the large number of possible examination areas and other boundary conditions, it follows that a large number of organ programs must be previously-defined, so that before the actual examination the doctor or medical assistant is faced with the task of selecting, from the large number of organ programs, the optimal organ program with the necessary post-processing parameters which are optimal for the purpose of the examination or organ to be examined, as applicable. This can sometimes be very demanding and difficult. With the variations in patient parameters, e.g. age, gender, weight, either additional organ programs must be provided or alternatively additional selection steps must be offered, which can have a negative effect on the workflow. In general there is a high risk of incorrect settings. The optimal image processing parameters even differ for different exposures.

In sum, for the doctor the manual and subjective selection method which has been the practice until now, with the multiplicity of individual different organ programs, is awkward, tedious and very easy to make mistakes with.

U.S. Pat. No. 6,064,775 A discloses an image processing device, by means of which image processing parameters can be determined, by reference to an image which has been made, for subsequent image recordings. For this purpose, the recorded image is analyzed and various analysis parameters determined, by reference to which the parameters for further processing are then determined.

SUMMARY OF INVENTION

An object of the invention is to specify a method which permits the automatic determination of one or more organ-dependent image postprocessing parameters.

This object is achieved by the claims.

In accordance with the invention, the automatic determination of the postprocessing parameters to be used for postprocessing the image is effected on the basis of the preprocessed image or the preprocessed image data, as applicable. The raw image data originally recorded is first corrected in relation to any offset, for example, as part of a normal image preprocessing procedure or an image preprocessing step, and in addition a gain correction is carried out, and also a defect correction. The various processing steps to be carried out as part of a normal image processing procedure are well known.

Starting from this preprocessed image or the data for the preprocessed image, as appropriate, a next step now determines a comparison image specific to the organ or alternatively the examination area, that is an image recorded at some earlier time for the same examination area on this or some other patient. This comparison image, recorded previously, has been optimally postprocessed using organ- or examination-area-specific postprocessing parameters, i.e. the postprocessing was carried out so that the maximum information content of the image was generated or was optimally extracted, as applicable. These comparison images are stored in a database, each with its set of postprocessing parameters, in the form of a group of images relating to a multitude of different examination areas. After the determination of a comparison image, relevant in relation to the originally recorded examination area or to the preprocessed image showing the examination area, the automatic postprocessing of the preprocessed raw image is carried out using the postprocessing parameters from the comparison image.

In doing this, the method in accordance with the invention is particularly advantageous in enabling the automatic acquisition of the optimal postprocessing parameters, and the automatic postprocessing. Unlike the prior art, the sole starting basis for the automatic determination of the parameters is the preprocessed raw image of the examination area, as a function of which the determination of the comparison image and determination of the parameters is carried out. The doctor or medical assistant is no longer required to determine manually and subjectively the required organ program with predefined image processing parameters, and possible sources of error associated with this are likewise excluded. The entire procedural sequence can be structured to be significantly faster, since corrections necessitated by errors are no longer required because the image postprocessing is always carried out on the basis of optimal postprocessing parameters determined beforehand, thus ensuring that in respect of image quality and image content the image which can be output is optimized by the processing. So optimal image processing is possible without the need for current information about the organ or the examination area, the patient, the exposure etc., because the sole basis for the selection is the preprocessed raw image data, and hence the content of the preprocessed image.

In a first alternative method variant, the determination of the relevant organ-specific comparison image can be made by a comparison of at least a part of the image data for the preprocessed image against the image data for the comparison images. As part of this comparison, something in the nature of a reconciliation is effected in respect of any agreements between the preprocessed image data or preprocessed image respectively and the postprocessed data for the comparison image or the postprocessed comparison image. The better the "match", that is the agreement between the current image and the optimally processed "historical" images, the more preferable it will be to use for the postprocessing the postprocessing parameters for the corresponding comparison image. Finally, the image postprocessing parameters for that "historical" image in the database which agrees most extensively with the currently recorded, preprocessed image will be used for postprocessing the latter image.

As part of a first embodiment of the invention, the comparison can then include the subtraction of the preprocessed image and the relevant comparison images from each other. That is, the degree of agreement can be determined by subtraction of the images. The smaller the difference between the preprocessed image and the postprocessed comparison image, the greater is the agreement between the images concerned. With this variant of the invention, the comparison image which has the least differences from the preprocessed image is best in agreement, its optimized postprocessing parameters are selected for the further processing.

An alternative method variant provides for the comparison to include the carrying out of an analysis of the preprocessed image to extract items of information relating to the organ shown in the image, with the comparison image being determination by reference to the result of the analysis. An approach which suggests itself for this purpose is the use of a suitable analysis algorithm, in particular a segmentation algorithm, by means of which the notable structures in the preprocessed image are determined as image-specific items of information. By reference to the structures so determined, and corresponding structures determined within the comparison images, the comparison is now carried out and the relevant comparison image with the best agreement is determined. From the analysis or segmentation algorithm certain bone structures are detected, for example, and these are then used as the basis for determining the comparison image.

Another alternative method for image comparison provides for an analysis of the preprocessed image to be carried out using a neural network, to extract items of information relating to the organ shown in the image, with the determination of the comparison image being made by reference to the result of the analysis. In the case of this alternative of the invention a neural network, trained by reference to the data for the optimally processed comparison images, analyzes the preprocessed image data which is given to it and as a result of the analysis outputs the relevant comparison image, the postprocessing parameters for which are then referred back to in the subsequent course of the method. The structure and manner of functioning of such neural networks is well known, so that there is no need to go into further details at this point. So no comparison of the data, between the current data and the data taken from the database, is necessary here.

Apart from the method, the invention relates in addition to an image postprocessing device, designed for carrying out the method, incorporating a computing device for processing image data, this computing device being designed to determine automatically an organ-specific postprocessed comparison image for a preprocessed organ-specific image, available to the computing device, on the basis of the image data for the preprocessed image, and the postprocessing parameters for the comparison image determined, and for the automatic postprocessing of the preprocessed image by reference to the post-processing parameters which have been determined.

Here, the computing device can contain a database containing a group of comparison images with assigned postprocessing parameters, from which database it is possible to read out a required comparison image together with or excluding its postprocessing parameters. However, the database need not be available in the computing device, but rather it can also be held externally to the device and each required comparison image or its postprocessing parameters, as applicable, can be downloaded from the external source.

As part of a first form of embodiment, the computing device can have an analysis facility, for comparing at least a part of the image data for the preprocessed image against the image data for the comparison image, and for determining the comparison image and the postprocessing parameters as a function of the result of the comparison. Here, the analysis facility can be designed as an image subtraction device for subtracting from each other the preprocessed image and each of the comparison images loaded from the database. Alternatively, the analysis facility can be designed, using an analysis algorithm and in particular a segmentation algorithm, to determine structures in the preprocessed image and to determine the relevant comparison image by reference to comparable structures in the comparison image.

One alternative to the carrying out of a data comparison provides for the analysis facility to be a neural network which analyzes the preprocessed image data and as the result of the analysis specifies the relevant comparison image together with or exclusive of the relevant postprocessing parameters.

Various parameters, used as part of the normal organ-dependent post-processing (incomplete list), are used as the postprocessing parameters. These are, for example, the look-up table (LUT), used in carrying out a gray-scale mapping with non-linear characteristic curves, which are designed to increase the contrast in the areas of the image which are of interest, and reduce it in areas of the image of less interest. A further postprocessing parameter is the so-called "edge-enhancement". This is a filtering method by which the original image is filtered using a specific high-pass filter and this filtered image is added, with an organ-dependent weighting factor, to the original image. In this way it is possible to improve the sharpness of the contours of objects. A further postprocessing parameter is the so-called "dynamic control", which is a dynamic contrast adjustment, also called harmonization. This is effected by filtering the original image using a low-pass filter, and this filtered image is subtracted, with a weighting factor, from the original image. In this way it is possible, for example in the case of a thorax image recording, to show the lungs and mediastinum in high contrast at the same time. It clearly follows that a group of different organ-specific postprocessing parameters must always be carried out for the organ which has been imaged or the examination area, but this is common knowledge.

Further advantages, characteristics and details of the invention ensue from the exemplary embodiment described below and by reference to the drawing.

BRIEF DESCRIPTION OF THE DRAWING

The drawing shows an image recording device for image processing according to the invention.

DETAILED DESCRIPTION OF INVENTION

The FIGURE shows an image recording device 1 incorporating an image recording facility 2 in the form of an X-ray device 3. The digital raw image data which is recorded is passed to an image processing device 4 in accordance with the invention, which incorporates a computing device 5, which performs the relevant image processing steps and generates from the raw image data passed to it a postprocessed image which can be output, and which is output on a monitor 6.

As described, the raw image data 7 is first passed from the X-ray device 3 to the image processing device 4. The image processing device 4 or the computing device 5, as applicable, has a facility or a device 8 for image preprocessing. As part of this image preprocessing, the raw image data supplied is preprocessed in respect, for example, of the offset, the gain and possible defects etc. as part of the normal pre-processing.

The preprocessed image or preprocessed image data, as applicable, is then passed to an analysis facility 9. This analysis facility 9 is in a position to determine for the image data or the organ, as applicable, specific, optimal image postprocessing parameters, which then form the basis for the postprocessing of the image.

The image analysis facility communicates with a database 10, in which are stored a multiplicity of different organ-specific comparison images 11 with their assigned organ-specific image postprocessing parameters 12. The comparison images 11 are organ-specific comparison images, which have been processed to be optimized using the assigned postprocessing parameters, i.e. the image postprocessing parameters have been so chosen and adjusted that the optimal postprocessed image is generated, with the maximum information and display content. In total, the comparison images make up all the relevant examination areas of a patient, insofar as they are required for the examinations undertaken with the X-ray device 3. For any one examination area, there can be not merely a single comparison image, but a multiplicity of different comparison images, relating to various patient parameters. For example, several different Thorax comparison images can be stored, deriving in each case from patients of different ages, or patients of different sizes etc., where specific postprocessing parameters would be required for each image in order to postprocess or retain it optimally, as applicable. Examples of the postprocessing parameters are a look-up table, parameters for edge-enhancement (EE) and parameters for dynamic contrast adjustment (DC). Further parameters can be present.

In conjunction with the database 10 and its contents, the analysis facility 9 is now in a position to determine, on the basis of the given preprocessed image data, the specific optimal postprocessing parameters for this image data. This can be effected in various ways, for which reason the analysis facility 9 can have different designs.

The analysis facility 9 can be a subtraction device which is capable of subtracting from one comparison image 11 at a time, read out from the database 10, the relevant preprocessed image data or preprocessed image which it is given. The comparison image for which the image subtraction gives the minimum difference value is the one which best agrees with the preprocessed image. When it is certain which comparison image 11 this is, the associated comparison image postprocessing parameters 12 are read out from the database 10 and together with the preprocessed image data are given to the facility or device 13 for image postprocessing, where the preprocessed image data is postprocessed, using the postprocessing parameters.

As an alternative to subtraction, the analysis facility 9 can also take the form of an analysis or segmentation algorithm, or incorporate one such, which is capable of recognizing relevant structures within the preprocessed image. For example, both lungs can be determined using the algorithm, and also further image data relating to them. By reference to the structures and data determined the analysis facility 9 then determines, by a comparison against corresponding structures and data extracted by the analysis facility 9 for each comparison image 11 which is loaded from the database 10, the comparison image 11 which best agrees. For this latter, the analysis facility 9 then determines the postprocessing parameters 12, and gives them to the facility or device 13 for image postprocessing.

As an alternative to this, the analysis facility 9 can also be a neural network which has been optimally trained beforehand by reference to the comparison images 11 present in the database 10. The preprocessed image data is passed to the input nodes of the neural network, and is then processed in the appropriate layers of the network. The ultimate result of the analysis by the neural network is the relevant comparison image 11, or directly the parameter set 12, required for the image postprocessing. Finally, by reference to the result of the analysis, the relevant postprocessing parameter set 12 which has been determined is read out from the database 10 and is passed via the analysis facility 9 to the facility or device 13 for image postprocessing. There, the automatic image processing and its output on the monitor 6 is carried out.

All in all, the method in accordance with the invention, or the use of an image processing device in accordance with the invention, as applicable, means that starting from the point in time when the raw image data is recorded there is absolutely no need for manual operations or subjective operations performed by a doctor, because the determination of the relevant, optimal organ-specific postprocessing parameters is effected completely automatically, as is the image postprocessing.

The invention claimed is:

1. A method for determining at least one organ-dependent parameter for medical image post-processing, comprising:
   recording a raw image, the raw image including an organ;
   using a computing device to perform the steps of:
      applying image preprocessing to the raw image for generating a preprocessed image;
      identifying an organ-specific comparison image stored in a comparison image database having a plurality of comparison images, the comparison images optimized by image postprocessing using organ-specific postprocessing parameters;
      acquiring the postprocessing parameters of the organ-specific comparison image; and
      postprocessing the preprocessed image using the postprocessing parameters,
   wherein comparing the preprocessed image to the comparison images includes mathematically subtracting the preprocessed image from the comparison image or mathematically subtracting the comparison images from the preprocessed image.

2. The method according to claim 1, wherein the organ-specific comparison image is identified by comparing at least part of the preprocessed image to the comparison images.

3. The method in accordance with claim 2, wherein comparing the preprocessed image to the comparison images includes analyzing the preprocessed image for generating information on the organ included in the postprocessing image, the generated information on the organ used for identifying the organ-specific comparison image.

4. The method in accordance with claim 3, wherein the information on the organ includes image structures present in the preprocessed image, and
   the organ-specific comparison image is identified by comparing the image structures to related image structures present in the comparison images.

5. The method in accordance with claim 4, wherein the image structures are determined using a segmentation algorithm.

6. The method according to claim 1, wherein the organ-specific comparison image is identified by analyzing the preprocessed image using a neural network trained by the comparison images, the analyzing generating information on the organ included in the preprocessed image.

7. An image processing device, comprising a computing device for processing image data, the computing device configured to:
   apply an image preprocessing algorithm to a raw image, the raw image including an organ, for generating a preprocessed image,
   identify an organ-specific comparison image stored in a comparison image database having a plurality of comparison images, the comparison images optimized by image postprocessing using organ-specific postprocessing parameters,
   acquire the postprocessing parameters of the organ-specific comparison image, and
   postprocess the preprocessed image using the postprocessing parameters,
   wherein the organ-specific comparison image is identified by comparing at least part of the preprocessed image to the comparison images,
   further comprising an analysis unit configured to:
      compare the preprocessed image to the comparison images,
      identify the organ-specific comparison image, and
      acquire the postprocessing parameters based on the comparison,
   wherein, for comparing the preprocessed image to the comparison images, the analysis unit is configured to mathematically subtract the pre-processed image from the comparison image or to mathematically subtract the comparison images from the preprocessed image.

8. The image processing device according to claim 7, further comprising a neural network trained by the comparison images, wherein the organ-specific comparison image is identified by analyzing the preprocessed image using the neural network, the analyzing generating information on the organ included in the preprocessed image.

9. The image processing device in accordance with claim 7, wherein the comparison images are stored in the comparison image database together with their related postprocessing parameters, the comparison image database configured to selectively read out the comparison images or the postprocessing parameters.

10. The image processing device in accordance with claim 7, wherein the analysis unit is configured to:
   determine image structures present in the preprocessed image, and
   determine the organ-specific comparison image by comparing the image structures to related image structures present in the comparison images.

* * * * *